United States Patent [19]

Seidel et al.

[11] Patent Number: 4,857,070

[45] Date of Patent: Aug. 15, 1989

[54] 2,4-DIAMINOPHENYL TETRAHYDROFURFURYL ETHERS, PROCESSES FOR THEIR PREPARATION AND TINTING COMPOSITIONS, WHICH CONTAIN THEM FOR KERATINIC FIBRES

[76] Inventors: Winfried Seidel, Fuchsrute 25, D-2087 Ellerbek; Horst Tappe, Dietzenbach, both of Fed. Rep. of Germany

[21] Appl. No.: 154,495

[22] Filed: Feb. 8, 1988

Related U.S. Application Data

[63] Continuation of Ser. No. 855,245, Apr. 24, 1986, abandoned.

[30] Foreign Application Priority Data

May 10, 1985 [DE] Fed. Rep. of Germany ....... 3516906

[51] Int. Cl.$^4$ ..................... A61K 7/13; C07D 305/04
[52] U.S. Cl. ............................ 8/408; 8/409; 8/410; 8/411; 8/412; 549/491
[58] Field of Search ................ 549/491; 8/405, 408, 8/411, 416

[56] References Cited

U.S. PATENT DOCUMENTS

| | | | |
|---|---|---|---|
| 3,981,677 | 9/1976 | Halasz et al. | 8/416 |
| 4,125,367 | 11/1978 | Bugaut et al. | 8/408 |
| 4,420,637 | 12/1983 | Bugaut et al. | 8/404 |

FOREIGN PATENT DOCUMENTS

| | | | |
|---|---|---|---|
| 2758203 | 7/1979 | Fed. Rep. of Germany | 8/411 |
| 0115853 | 9/1980 | Japan | 549/491 |

*Primary Examiner*—Glennon H. Hollrah
*Assistant Examiner*—Susan P. Treanor
*Attorney, Agent, or Firm*—Beveridge, DeGrandi & Weilacher

[57] ABSTRACT

The invention relates to new 2,4-diaminophenyl tetrahydrofurfuryl ethers of the general formula VIII and to their salts with inorganic or organic acids

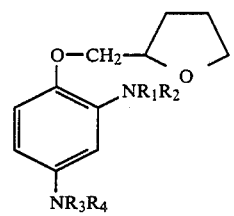

(VIII)

in which $R_1$, $R_2$, $R_3$ and $R_4$, independently of one another, each represent a hydrogen atom, a $(C_1$–$C_4)$alkyl group, hydroxy$(C_2$–$C_4)$alkyl group, dihydroxy$(C_3$–$C_4)$alkyl group, halogeno$(C_2$–$C_4)$alkyl group, amino$(C_2$–$C_4)$alkyl group or an amino$(C_2$–$C_4)$alkyl group which is substituted once or twice by methyl, ethyl or hydroxyethyl radicals on the nitrogen, the carbon chain having a straight or branched arrangement, and it being a proviso that at least one of $R_1$, $R_2$, $R_3$ and $R_4$ represents a hydrogen atom, to processes for their preparation, and to aqueous tinting compositions for keratin fibres such as fur and human hair, containing at least one coupler and at least one developing component together with customary additives and auxiliaries, the coupler corresponding to the general formula VIII or to the acid salts of these compounds.

13 Claims, 7 Drawing Sheets

2,4-DIAMINOPHENYL TETRAHYDROFURFURYL ETHERS, PROCESSES FOR THEIR PREPARATION AND TINTING COMPOSITIONS, WHICH CONTAIN THEM FOR KERATINIC FIBRES

This application is a continuation of prior application Ser. No. 855,245 filed on Apr. 24, 1986, now abandoned.

The invention relates to new 2,4-diaminophenyl tetrahydrofurfuryl ethers, to processes for their preparation and to tinting agents for keratinic fibres, specifically for fur and human hair, which contain them.

For the tinting of hair particular importance attaches to the so-called oxidation dyes which are formed by oxidative coupling of developing components (such as, for example, p-phenylenediamines, p-aminophenols, p-diaminopyridines etc.) with coupling components (such as, for example, phenols, resorcinols, m-aminophenols, m-phenylenediamines, naphthols, pyrazoles, etc), since they are formed under the boundary conditions of the techniques of use (low tinting temperature and short tinting time, for example) already in intense shades and with very good fastness properties.

Oxidation dyes likewise play an important part in the tinting of furs.

Good oxidation dye precursors must primarily meet the following requirements of the technique of use:

On oxidative coupling with the particular coupling or developing components they must provide the desired colour, which ought to have good absorptive capacity and levelling power on hair or fur, in adequate intensity. The dyes which are formed must be, in general, stable and, in particular, resistant to washing, light, sweat and heat. In particular, under the conditions of wear they must not be prone to shifts in the original colour shade.

Furthermore, they ought to be toxicologically and dermatologically acceptable.

These requirements cannot always be reconciled. This is particularly evident in the area of the so-called blue couplers. The state of the art for these is represented by 2,4-diaminoanisole, which is a compound which, on the one hand, is almost entirely satisfactory for the technique of use but, on the other hand, is toxicologically controversial.

At the present time, some 2,4-diaminophenyl ethers have already been proposed to replace 2,4-diaminoanisole. However, the compounds described in German Offenlegungsschriften Nos. 2,737,138, 3,016,109 and 3,016,881 are not yet satisfactory since, on the one hand, their tinting and fastness properties are inferior to those of 2,4-diaminoanisole and, on the other hand, they can be prepared with economy.

One aim of the present invention is thus to make available new compounds as blue couplers which (a) are completely satisfactory as dyes, (b) are toxicologically acceptable, and (c) can be prepared with economy similar to that for 2,4-diaminoanisole and its derivatives.

Blue couplers which meet these requirements are the compounds of the general formula VIII and their salts with inorganic or organic acids,

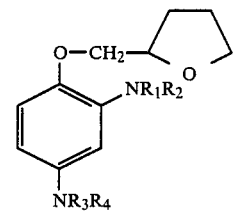

(VIII)

in which $R_1$, $R_2$, $R_3$ and $R_4$, independently of one another, each represent a hydrogen atom, a $(C_1-C_4)$-alkyl group, hydroxy$(C_2-C_4)$alkyl group, dihydroxy$(C_3-C_4)$alkyl group, halogeno$(C_2-C_4)$alkyl group, amino$(C_2-C_4)$alkyl group or an amino$(C_2-C_4)$alkyl group which is substituted once or twice by methyl, ethyl or hydroxyethyl radicals on the nitrogen, the carbon chain having a straight or branched arrangement.

Of these compounds 2,4-diaminophenyl tetrahydrofurfuryl ether of the formula XI and its acid salts meet the said requirements to a particularly high degree.

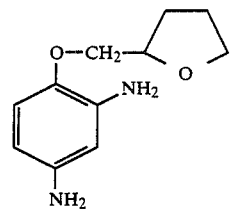

(XI)

Other examples for compounds of the general formula VIII are shown in Table I.

TABLE I

| preferred meanings of the radicals $R_1$, $R_2$, $R_3$ and $R_4$ in the compounds of the general formula VIII | | | |
|---|---|---|---|
| $R_1$ | $R_2$ | $R_3$ | $R_4$ |
| $R_3$ | $R_4$ or | $R_1$ | $R_2$ |
| H | H | H | H |
| $CH_3$ | H | H | H |
| $CH_2CH_3$ | H | H | H |
| $CH_2CH_2CH_3$ | H | H | H |
| $CH-CH_3$ <br> \|  <br> $CH_3$ | H | H | H |
| $CH_2CH_2CH_2CH_3$ | H | H | H |
| $CH-CH_2CH_3$ <br> \| <br> $CH_3$ | H | H | H |

TABLE I-continued preferred meanings of the radicals $R_1$, $R_2$, $R_3$ and $R_4$ in the compounds of the general formula VIII

| $R_1$ / $R_3$ | $R_2$ / $R_4$ | or | $R_3$ / $R_1$ | $R_4$ / $R_2$ |
|---|---|---|---|---|
| CH$_2$—CH(CH$_3$)—CH$_3$ | H | | H | H |
| CH$_2$CH$_2$—OH | H | | H | H |
| CH$_2$CH$_2$CH$_2$—OH | H | | H | H |
| CH$_2$—CH(OH)—CH$_3$ | H | | H | H |
| CH(CH$_3$)—CH$_2$—OH | H | | H | H |
| CH$_2$—CH(OH)—CH$_2$CH$_3$ | H | | H | H |
| CH$_2$CH$_2$—CH(OH)—CH$_3$ | H | | H | H |
| CH(CH$_2$CH$_3$)—CH$_2$—OH | H | | H | H |
| CH$_2$—CH(OH)—CH$_2$(OH) | H | | H | H |
| CH$_2$CH$_2$—Br | H | | H | H |
| CH$_2$CH$_2$—NH$_2$ | H | | H | H |
| CH$_2$CH$_2$CH$_2$—NH$_2$ | H | | H | H |
| CH$_2$—CH(NH$_2$)—CH$_3$ | H | | H | H |
| CH$_3$ | CH$_3$ | | H | H |
| CH$_3$ | CH$_2$CH$_2$—OH | | H | H |
| CH$_3$ | CH$_2$CH$_2$CH$_2$—OH | | H | H |
| CH$_3$ | CH$_2$CH$_2$—OH | | H | H |
| CH$_2$CH$_3$ | CH$_2$CH$_3$ | | H | H |
| CH$_2$CH$_3$ | CH$_2$CH$_2$—OH | | H | H |
| CH$_2$CH$_3$ | CH$_2$CH$_2$CH$_2$—OH | | H | H |
| CH$_2$CH$_2$—OH | CH$_2$CH$_2$—OH | | H | H |
| CH$_3$ | H | | CH$_3$ | H |
| CH$_3$ | CH$_2$CH$_2$—OH | | CH$_3$ | H |
| CH$_3$ | H | | CH$_2$CH$_2$—OH | H |
| CH$_3$ | H | | CH$_2$CH$_2$—OH | CH$_2$—OH |
| CH$_3$ | H | | CH$_2$CH$_2$—OH | H |
| CH$_3$ | H | | CH$_2$CH$_2$—NH | H |
| CH$_3$ | CH$_3$ | | CH$_2$—OH | H |
| CH$_3$ | CH$_3$ | | CH$_2$CH$_2$—NH$_2$ | H |
| CH$_3$ | CH$_3$ | | CH$_2$—CH(OH)—CH$_2$(OH) | H |
| CH$_2$CH$_3$ | H | | CH$_2$CH$_3$ | H |
| CH$_2$CH$_3$ | CH$_2$CH$_2$—OH | | CH$_2$CH$_3$ | H |
| CH$_2$CH$_3$ | H | | CH$_2$CH$_2$—OH | H |
| CH$_2$CH$_3$ | H | | CH$_2$CH$_2$—OH | CH$_2$CH$_2$—OH |
| CH$_2$CH$_3$ | H | | CH$_2$CH$_2$—OH | H |
| CH$_2$CH$_3$ | H | | CH$_2$CH$_2$—NH$_2$ | H |
| CH$_2$CH$_3$ | CH$_2$CH$_3$ | | CH$_2$CH$_2$—OH | H |
| CH$_2$CH$_3$ | CH$_2$CH$_3$ | | CH$_2$CH$_2$—NH$_2$ | H |
| CH$_2$CH$_3$ | CH$_2$CH$_3$ | | CH$_2$—CH(OH)—CH$_2$(OH) | H |
| CH$_2$CH$_2$CH$_3$ | H | | CH$_2$CH$_2$—OH | H |
| CH$_2$CH$_2$CH$_3$ | CH$_2$CH$_2$—OH | | CH$_2$CH$_2$—OH | H |
| CH$_2$CH$_2$CH$_3$ | H | | CH$_2$CH$_2$—OH | CH$_2$CH$_2$—OH |

TABLE I-continued preferred meanings of the radicals $R_1$, $R_2$, $R_3$ and $R_4$ in the compounds of the general formula VIII

| $R_1$ / $R_3$ | $R_2$ / $R_4$ | or | $R_3$ / $R_1$ | $R_4$ / $R_2$ |
|---|---|---|---|---|
| $\begin{array}{c}CH-CH_3\\|\\CH_3\end{array}$ | H | | $CH_2CH_2-OH$ | H |
| $\begin{array}{c}CH-CH_3\\|\\CH_3\end{array}$ | $CH_2CH_2-OH$ | | $CH_2CH_2-OH$ | H |
| $\begin{array}{c}CH-CH_3\\|\\CH_3\end{array}$ | H | | $CH_2CH_2-OH$ | $CH_2CH_2-OH$ |
| $\begin{array}{c}CH_2-CH-CH_3\\|\\CH_3\end{array}$ | H | | $CH_2CH_2-OH$ | H |
| $\begin{array}{c}CH_2-CH-CH_3\\|\\CH_3\end{array}$ | $CH_2CH_2-OH$ | | $CH_2CH_2-OH$ | H |
| $\begin{array}{c}CH_2-CH-CH_3\\|\\CH_3\end{array}$ | H | | $CH_2CH_2-OH$ | $CH_2CH_2-OH$ |
| $CH_2CH_2-OH$ | H | | $CH_2CH_2-OH$ | H |
| $CH_2CH_2-OH$ | H | | $CH_2CH_2-OH$ | $CH_2CH_2-OH$ |
| $\begin{array}{c}CH_2-CH-CH_2\\|\quad\;\;|\\OH\;\;\;OH\end{array}$ | H | | $CH_2CH_2-OH$ | H |
| $CH_2CH_2-Br$ | H | | $CH_2CH_2-Br$ | H |
| $CH_2CH_2-NH_2$ | H | | $CH_2CH_2-NH_2$ | H |
| $CH_2CH_2-N(CH_3)_2$ | $CH_2CH_2-N(CH_3)_2$ | | H | H |

The processes for the preparation of the compounds of the general formula VIII are summarized in the diagram which follows. In this diagram the individual process stages are provided with letters (A, B, C, D, E and F) identifying the reaction type. In the description which follows the general processes by which the individual stages are carried out are explained in detail under these identification letters.

| Coupler Formula | COUPLER K-1<br>Formula XI | COUPLER K-2<br>Formula XII | COUPLER K-5<br>Formula XIV | | |
|---|---|---|---|---|---|
| Name | 2,4-Diaminophenyl-tetrahydrofurfuryl-ether | 2-(β-Hydroxyethyl-amino)-4-aminophenyl-tetrahydrofurfuryl-ether | 2-Amino-4-bis(β-hydroxyethyl)amino-phenyl-tetrahydro-furfurylether | 2-Amino-4-acetyl-aminophenyltetra-hydrofurfuryl ether | 2-Amino in which one hydrogen is replaced by —CH$_2$COOC$_2$H$_5$ |
| Identity | invention | invention | invention | Mitsui (Ia) | Mitsui (IIa) |
| COLOR | | | | | |
| Color tone | blue black | dark blue | blue gray | smokey medium blonde | light blonde |
| Depth of color | 1 | 2 | 5 | 7 | 8 |
| Evaluation of the coloring | Outstanding<br>very good blue<br>fulfill the objects of invention | | good blue coupler | no blue coupler<br>do not fulfill the objects of the invention, useless compounds | |

Depth of Color: Scale from 1-10 (1 = highest possible, optimum color depth, 10 = practically no depth of color, useless
Developer: 2,5-Diaminotoluol; introduced amounts coupler and developer; each 0.005 mol (developer = E2)

A. General processes for the preparation of 2-nitrophenyl tetrahydrofurfuryl ethers of the formulae II or V and VI, which are substituted in the 4-position, by halogen replacement The compounds of the formulae II or V and VI can be prepared by methods which are customary per se for the synthesis of phenyl ethers from activated halogenobenzenes and alcohols, such as are indicated, for example, in Houben-Weyl, Methoden der Organischen Chemie (Methods of Organic Chemistry, edited by E. Müller), Georg Thieme Verlag, Stuttgart, in volume IV/3 (1965) on pages 75-79 and in volume V/4 (1960) on pages 704-709, from a 2,4-dinitrohalogenobenzene or from the fluoronitroaniline derivatives of the general formula VII and tetrahydrofurfuryl alcohol.

In general, a 2,4-dinitrohalogenobenzene or the compounds of the general formula VII are reacted, at temperatures between room temperature and 120° C., with tetrahydrofurfuryl alcohol, which can also be used in excess, in the presence of a base to give the compounds of the formulae II or V and VI, it being possible for the reaction to take place in the presence or absence of inert solvents. Suitable bases for binding the hydrogen halide eliminated during the reaction are alkali metal hydroxides, bicarbonates and carbonates, alkaline earth metal oxides, hydroxides, bicarbonates and carbonates, as well as tertiary organic nitrogen bases.

For example, it is possible initially to fuse 2,4-dinitrobenzene together with sodium carbonate at 70° C., and gradually to add, and react with, small portions of tetrahydrofurfuryl alcohol, and subsequently to isolate the 2,4-dinitrophenyl tetrahydrofurfuryl ether of the formula II.

A preferred embodiment of the process for the preparation of 2,4-dinitrophenyl tetrahydrofurfuryl ether, in which there is complete reaction and formation of particularly small amounts of by-products, comprises dissolution of 2,4-dinitrochlorobenzene in excess tetrahydrofurfuryl alcohol and addition, at about 40° C., of an excess, amounting to 10-20 mol%, of sodium hydroxide beads in portions. After the reaction is complete, the 2,4-dinitrophenyl tetrahydrofurfuryl ether which results as an oil can be obtained as a crystalline substance by trituration with water, removal of the water and further washing with fresh water. In an advantageous manner, the product obtained after the first wash with water, which is still oily, can also be taken up in an inert organic solvent.

The preparation of the compounds of the formulae V and VI from the fluoronitroaniline derivatives of the general formula VII can be carried out in an analogous manner.

B. General processes for the preparation of 2-amino-4-nitrophenyl tetrahydrofurfuryl ether of the formula III and of 4-amino-2-nitrophenyl tetrahydrofurfuryl ether of the formula V by partial reduction of 2,4-dinitrophenyl tetrahydrofurfuryl ether 2,4-Dinitrophenyl tetrahydrofurfuryl ether of the formula II is reduced with alkali metal or ammonium hydrogen sulphide or polysulphide at pH values from 5 to 11, preferably from 9 to 11, and temperatures between room temperature and the boiling point of the reaction mixture, preferably between 60° and 90° C., mainly to give 2-amino-4-nitrophenyl tetrahydrofurfuryl ether of the formula III.

The preferred reaction medium is water, but it is also possible to use (additional) organic solvents such as, for example, alcohols or ethers which are miscible with water. If the reaction, which is always carried out under protective gas (nitrogen, argon or the like), substantially takes place in water, it proceeds in two phases; it is then advisable to add emulsifiers. In a general embodiment, the compound of the formula II is initially introduced in the solvent, and the reducing agent is metered in under protective gas at the selected reaction temperature. If the pH increases to a value >11 during this, the reaction mixture can be maintained at a pH between 9 and 11 by addition of a compound with an acid reaction. For working up, the organic solvent is removed where appropriate, the mixture is cooled to about 0° to 10° C., and the precipitated reaction product is separated off. For purification, it can be triturated with diethyl ether and isolated as the residue. The ethereal mother liquor is then used to obtain the compound of the formula V.

This process provides the compounds of the formulae III and V in the ratio of approximately 3:1. It is also possible to obtain a mixture of the compounds of the formulae III and V by catalytic reduction of the compound of the formula II. For this purpose, it is necessary to stop the reaction after uptake of the amount of hydrogen necessary for the reduction of one nitro group (of the compound II). Customary catalysts such as, for example, Raney nickel, palladium on active charcoal and platinum on active charcoal are used. The reaction temperature is between room temperature and 100° C., preferably between 40° C. and 70° C., and the pressure is between atmospheric pressure and 100 bar, preferably between 10 and 50 bar. The solvents used are customary solvents such as, for example, water, toluene, glacial acetic acid, lower alcohols and ether compounds. For isolation of the reaction mixture, the catalyst is separated off, and the solvent is entirely removed in vacuo. To separate the mixture, used is made of the different solubilities of the two compounds in organic solvents (compound III is essentially less soluble than compound V). Thus, for example, on recrystallization of a mixture of the compounds III and V from toluene or ethanol the pure compound III is obtained, while the isomeric compound V is to be found entirely in the mother liquors. A particularly advantageous way of separating compounds III and V is to triturate the mixture (where appropriate repeatedly) with ether (in about a 2-10-fold amount). Whereas the compound III is almost completely insoluble in ether and can be filtered off, the mother liquor contains all the, highly enriched, compound V which can likewise be obtained pure in a preparatively worthwhile amount by subsequent column chromatography on silica gel using a suitable mobile phase (for example toluene/2-butanol in the ratio 7:3). (If the requirements on purity are less, it is perfectly adequate to evaporate the ethereal mother liquor and subsequently to use the highly enriched compound V).

It would normally have been expected that two selective processes would be needed in order to obtain, on the one hand, the compound III and, on the other hand, the compound V, and thus also the series of compounds IV and VI respectively. It is remarkable that the mixture of the compounds III and V, which is easy to obtain, represents a good basis for this, since despite the great similarity of the two compounds it is possible, surprisingly, by treatment with solvents, specifically ether, to separate the mixture in a straightforward manner so that both compounds III and V can be separately used further for preparations.

C. General processes for the preparation of 4-nitrophenyl tetrahydrofurfuryl ethers of the general formula IV, which are substituted in the 2-position, and of 2-nitrophenyl tetrahydrofurfuryl ethers of the general formula VI, which are substituted in the 4-position, by alkylation Alkylation of the compounds of the formulae III and V for the preparation of the compounds of the formulae IV and VI is carried out by methods known per se. It is possible to use as alkylating agents which contain the radicals $R_1$ or $R_2$ and $R_3$ or $R_4$, and which are generally used in excess, epoxides, specifically ethylene oxide, dialkyl sulphates, alkyl halides, hydroxyalkyl halides, dihydroxyalkyl halides, halogenoalkyl halides, aminoalkyl halides and aminoalkyl halides which are substituted once or twice with methyl, ethyl or hydroxyethyl groups on the nitrogen (the amino group optionally being protected, and the protecting group being eliminated after the alkylation).

The solvents which are used are water, protic or aprotic organic solvents such as, for example, ($C_1$–$C_4$)alcohols, dimethylformamide, N-methylpyrrolidone or ethers such as, for example, ethylene glycol dimethyl ether, diethylene glycol dimethyl ether, tetrahydrofuran or dioxane.

Suitable acid-binding agents are bases such as alkali metal hydroxides, bicarbonates and carbonates, alkaline earth metal oxides, hydroxides, bicarbonates and carbonates, as well as tertiary organic amines.

The compound which is to be alkylated (III or V) is initially introduced into the solvent (where appropriate together with the acid-binding agent) and the alkylating agent is metered in at temperatures between room temperature and the reflux temperature, preferably between 60° C. and the reflux temperature. In this process, the acid-binding agent can either also be introduced initially or added in parallel with the alkylating agent. After the reaction is complete, the product is isolated by, for example, addition of water and extraction by stirring or removal of the salts and subsequent evaporation of the reaction mixture.

For the purpose of monoalkylation, the amino group of the compound which is to be alkylated (III or V) is optionally provided before the alkylation with an auxiliary group such as, for example, a tosyl group which is eliminated again after alkylation has taken place. The derivative obtained after a monoalkylation can then again be reacted, as described, with another of the said alkylating agents.

D. General processes for the preparation of the carbamates of the formulae IX, X, XIII, XV and XVI by reaction with β- or γ-halogeno($C_2$–$C_4$)alkyl chloroformates For the preparation of the carbamates of the formulae IX, X, XIII, XV and XVI, the compounds of the formulae II, V, xII, XIV and XI respectively are initially introduced into an inert organic solvent, such as, for example, toluene, chlorobenzene, methyl ethyl ketone, dioxane, ethylene glycol dimethyl ether or diethylene glycol dimethyl ether, and the mixture is heated to a temperature between room temperature and the reflux temperature, preferably between 70° C. and the reflux temperature. The β- or γ-halogeno($C_2$–$C_4$)alkyl chloroformate is then metered in, in equimolar amount or in slight excess or, in the case of the 2,4-diaminophenyl tetrahydrofurfuryl ether XI for the preparation of the bis-carbamate of the general formula XVI, in twice the molar amount or in slight excess. In this process it is possible for an acid-binding agent—the bases already mentioned under C. are suitable—either to be initially introduced to or added in parallel to the chloroformic ester which has already been mentioned. After reaction is complete, the carbamates are isolated by (a) addition of water and stirring the mixture in the cold or (b) removal of the inorganic salts by filtration and partial or complete removal of the solvent in vacuo.

E. General processes for the preparation of the hydroxyalkyl compounds of the formulae IV, VI and VIII, by treatment with base By treatment with strong bases—suitable for this are alkali metal or alkaline earth metal hydroxides, preferably 10–50% strength aqueous sodium or potassium hydroxide solution—the carbamates of the formulae IX, X, XIII, XV and XVI are converted into the hydroxyalkyl compounds of the formulae IV, VI and VIII.

Two procedures are convenient: (a) the carbamate of the formula IX, X, XIII, XV or XVI is initially introduced in water or an organic solvent such as, for example, a ($C_1$–$C_4$)-alcohol, an ether which is miscible with water or mixtures thereof; then, at room temperature, approximately the calculated amount of alkali, that is to say 3 moles of alkali per mole of carbamate and 6 moles of alkali per mole of bis-carbamate, is metered in, and the mixture is then stirred until reaction is complete, it being possible where appropriate to heat to reflux. (b) The alkali, which can be diluted with the said solvents, is initially introduced, the carbamate of the formula IX, X, XIII, XV or XVI is metered in, in pure form or dissolved in one of the said organic solvents, at a temperature between room temperature and about 70° C., and then the mixture is stirred until reaction is complete. With both variants it is possible for the working up of the reaction solution, which has a pH of about 12–14, to reduce the pH to about 7 to about 10, by addition of an organic or inorganic acid. The inorganic salts are then separated off, water is added where appropriate, and the product of the formula IV, VI or VIII is isolated after the organic solvent has been removed.

For the preparation of the hydroxyalkyl compounds of the formula VIII, the process which has been described is advantageously carried out under a protective gas such as, for example, nitrogen or argon, and the products are isolated in the form of their salts with inorganic or organic acids, such as, for example, as chlorides, sulphates, phosphates, acetates, propionates, lactates or citrates.

F. General processes for the preparation of the 2,4-diaminophenyl tetrahydrofurfuryl ethers of the formulae XI or XII and XIV by reduction The preparation of the 2,4-diaminophenyl tetrahydrofurfuryl ethers of the formulae XI or XII and XIV can be carried out by reduction of the 2,4-dinitrophenyl tetrahydrofurfuryl ether II or of the aminonitrophenyl tetrahydrofurfuryl ethers of the general formulae IV and VI using base metals or by catalytic reduction.

Customary catalysts are used for the catalytic reduction, such as, for example, Raney nickel, palladium on active charcoal or platinum on active charcoal. The reaction temperature is between room temperature and 120° C., preferably between 40° C. and 100° C., and the pressure is between atmospheric pressure and 100 bar, preferably between 20 and 70 bar. The solvents which are used are customary solvents such as, for example, water, toluene, glacial acetic acid, lower alcohols, and ether compounds. After reduction has taken place and the catalyst has been removed, the product of the formula XI, XII or XIV can be isolated in a free form by removal of the solvent under a reduced pressure of a protective gas, but it is preferably converted into a salt—likewise under a protective gas—by addition of approximately the equivalent amount of an acid, the salt either being precipitated immediately or obtained after removal of the solvent in vacuo. The salts which are suitable for this are those already mentioned under E. In the case of 2,4-diaminophenyl tetrahydrofurfuryl ether XI, isolation of the salt $XI \times \frac{1}{2}H_2SO_4$, which is produced in high yield and purity, has proved to be especially advantageous.

The invention is illustrated by the examples which follow:

EXAMPLE 1

Preparation of 2,4-diaminophenyl tetrahydrofurfuryl ether of the formula XI

A. Preparation of 2,4-dinitrophenyl tetrahydrofurfuryl ether of the formula II as intermediate:

202.5 g of 2,4-dinitrochlorobenzene are melted at 70° C. and 100 g of sodium carbonate and 105 g of tetrahydrofurfuryl alcohol are added successively. The mixture is then heated at 130° C. for 20 hours, cooled to 100° C., 1 l of water is added, and the mixture is cooled to room temperature with stirring. The aqueous phase is decanted off, and to remove a small amount of starting compound from the remaining oil it is stirred with 4 g of sodium hydroxide prills at 40° C. for a few hours, and washed four times with 200 ml of water each time, carefully separated off and dried in a vacuum oven at 40° C. 182 g of an oil (68% of the theoretical figure) are obtained, and this completely crystallizes after some time.

Melting point: 51°-52° C.

B. Preparation of 2,4-diaminophenyl tetrahydrofurfuryl ether of the formula XI:

469 g of the compound of the formula II prepared according to A. are placed in a 5 l stainless steel autoclave together with 3 l of methanol and about 20 g of Raney nickel catalyst, and catalytic hydrogenation is carried out at 70°-80° C. and under a hydrogen pressure of about 80 bar within about 2 hours. The catalyst is filtered off under nitrogen, and gaseous hydrogen chloride is passed in to the methanolic filtrate until saturated. The solution is evaporated in vacuo to a volume of 2.5 l, 1.5 l of ether are added, and the product which precipitates out as the dihydrochloride is filtered off with suction and dried in vacuo.

Yield: 430 g (87.4% of theory).
Melting point: 226°-230° C.

EXAMPLE 2

Preparation of 2,4-diaminophenyl tetrahydrofurfuryl ether of the formula XI

A. Preparation of 2,4-dinitrophenyl tetrahydrofurfuryl ether of the formula II as intermediate:

A.1. 2025 g of 2,4-dinitrochlorobenzene are dissolved in 3000 ml of tetrahydrofurfuryl alcohol at 40° C. and, within about 2.5 hours, 440 g of sodium hydroxide in the form of prills are added, the temperature being maintained at 40°-45° C. by cooling in ice. After 1 hour, if necessary to complete the reaction, an additional 40 g of sodium hydroxide prills added in portions. After a further hour, the mixture is washed twice with 2 l and twice with 1 l of water, whereupon the product crystallizes out. It is filtered off, washed with a little water, and dried in a vacuum oven at 40° C.

Yield: 2306 g (86% of the theoretical figure).
Melting point: 55° C.
IR spectrum: see FIG. 1.

A.2. A reaction is carried out as described in A.1. However, for the working up, only two washings with 2 l of water are carried out, and the wash water is carefully separated off, and the remaining oil is dried in a vacuum oven at 40° C.

Yield: 2363 g (88.2% of the theoretical figure).

B. Preparation of 2,4-diaminophenyl tetrahydrofurfuryl ether of the formula XI:

804 g of the compound of the formula II prepared according to A.1. or A.2. are stirred into 6 l of toluene, and the mixture is transferred into a 10 l stainless steel autoclave, 8 g of palladium on charcoal (5% strength) are added as catalyst, and catalytic hydrogenation is carried out at 100° C. and under a hydrogen pressure of 70 bar within 5 hours. The pressure is released from the autoclave at 70° C., and it is opened, the catalyst, which can be re-used, is removed by filtration under nitrogen, and 150 g of 100% strength sulphuric acid are added to the toluene solution at 60°-70° C. within about 30 minutes, and the product is extracted by stirring as the temperature falls, and is filtered off with suction, washed with 1 l of toluene and dried in a vacuum oven at 70° C.

Yield: 677 g (87.8% of theory).
Melting point: 216°-218° C.
Elemental analysis for $C_{11}H_{16}N_2O_2 \times \frac{1}{2}H_2SO_4$:

|  | C | H | N | S | O |
|---|---|---|---|---|---|
| Calculated: | 52.35% | 6.66% | 10.89% | 6.23% | 24.87% |
| Found: | 51.2% | 6.6% | 11.1% | 6.5% | 24.8% |

Sulphate content: calculated: 19.06% found: 19.3%.
IR spectrum: see FIG. 10

EXAMPLE 3

Preparation of 4-amino-2-(β-hydroxyethyl)aminophenyl tetrahydrofurfuryl ether

A. Preparation of 2-amino-4-nitrophenyl tetrahydrofurfuryl ether of the formula III as intermediate I:

3 drops of emulsifier Emulsogen EL are added to 161 g of 2,4-dinitrophenyl tetrahydrofurfuryl ether in 750 ml of water and, within about 2 hours, 195 g of 32 percent by weight sodium hydrogen sulphite solution is added dropwise at 70°-80° C. under nitrogen. During this, the pH increases from about 5-6 to 11, and it is then maintained at 10-11 by addition of a few drops of concentrated hydrochloric acid. After 1 hour, the mixture is cooled to 10° C., and the product is filtered off with suction, washed with 300 ml of water, dried, triturated with 400 ml of diethyl ether, again filtered off with suction, and dried.

Yield: 90 g (63% of the theoretical figure).
Melting point: 144°-145° C.
IR spectrum: see FIG. 2.

B. Preparation of 2-(β-chloroethoxycarbonyl)amino-4-nitrophenyl tetrahydrofurfuryl ether as intermediate II:

36 g of β-chloroethyl chloroformate are added dropwise to 59.5 g of 2-amino-4-nitrophenyl tetrahydrofurfuryl ether of the formula III, prepared above under A., and 14 g of calcium carbonate in 250 ml of dioxane at 70° C. The mixture is then stirred at 75° C. for 1 hour, and the inorganic salts are removed at elevated temperature, and the major amount of the product is allowed to crystallize out of the filtrate. A second precipitate is obtained by extensive evaporation of the mother liquor. Total yield: 72.3 g of 2-(β-chloroethoxycarbonyl)amino-4-nitrophenyl tetrahydrofurfuryl ether (84% of the theoretical figure).

Melting point: 125°–126° C.

IR spectrum: see FIG. 6.

C. Preparation of 2-(β-hydroxyethyl)amino-4-nitrophenyl tetrahydrofurfuryl ether as intermediate III:

68.9 g of the 2-(β-chloroethoxycarbonyl)amino-4-nitrophenyl tetrahydrofurfuryl ether, obtained above under B., are introduced, at 50° C., into a mixture of 60 g of 40 percent by weight aqueous sodium hydroxide solution and 150 ml of ethanol, the temperature being maintained at 50° C. to 60° C. The mixture is then stirred without further heating for 30 minutes, and then the pH is adjusted to 8 with concentrated hydrochloric acid, and the mixture is filtered, the filtrate is evaporated to dryness, and the residue is taken up in ethanol to remove residual salts, and the mixture is again filtered, the solvent is removed in vacuo, and in this way an oil which is induced to crystallize by trituration with 200 ml of ether is obtained. Yield: 36 g (65.8% of the theoretical figure) of 2-(β-hydroxyethyl)amino-4-nitrophenyl tetrahydrofurfuryl ether.

Melting point: 71° C.

IR spectrum: see FIG. 7.

D. Preparation of 4-amino-2-(β-hydroxyethyl)aminophenyl tetrahydrofurfuryl ether:

56.4 g of the intermediate III prepared according to C. are transferred together with 160 ml of ethanol into a stainless steel autoclave, about 1 g of Raney nickel catalyst is added, and catalytic reduction is carried out within 4 hours at 70° C. and under a hydrogen pressure of 80 bar. After removal of the catalyst, the reaction solution is acidified with sulphuric acid under nitrogen, and the product is isolated as the sulfuric acid salt ($\times \frac{1}{2}H_2SO_4$).

Yield: 40.3 g (67% of theory).

Melting point: 127°–128° C.

IR spectrum: see FIG. 11.

EXAMPLE 4

Preparation of 2-amino-4-(β-hydroxyethyl)aminophenyl tetrahydrofurfuryl ether

A. Preparation of 4-amino-2-nitrophenyl tetrahydrofurfuryl ether of the formula V as intermediate I:

A.1. The ethereal mother liquor produced in Example 3, stage A. is evaporated to dryness and purified by column chromatography on silica gel (toluene/2-butanol (7:3)). 30 g (21% of the theoretical figure) of the desired product are obtained in the form of a dark reddish-yellow oil.

A.2. 78 g of 4-fluoro-3-nitroaniline are initially introduced into 150 g of tetrahydrofurfuryl alcohol and, at 40°–60° C., 24 g of sodium hydroxide prills are added within 1 hour. After 3 hours at 60° C., the mixture is cooled to room temperature, inorganic salts are removed by filtration with suction, trituration with water is carried out three times with 500 ml each time, and the remaining oil is carefully separated off and dried.

Yield: 103 g (86.5% of the theoretical figure).

IR spectrum: see FIG. 3.

B. Preparation of 4-(β-chloroethoxycarbonyl)amino-2-nitrophenyl tetrahydrofurfuryl ether as intermediate II:

36 g of β-chloroethyl chloroformate are added dropwise to 59.5 g of 4-amino-2-nitrophenyl tetrahydrofuryl ether of the formula V (obtainable according to A.1. or A.2.) and 14 g of calcium carbonate in 200 ml of 1,2-dimethoxyethane at 70° C. The mixture is then stirred at 80° C. for 1 hour, the inorganic salts are removed at elevated temperature, and the filtrate is evaporated to dryness. The remaining oil completely crystallizes after a short time; the crystals are triturated with 50 ml of ether, filtered off with suction, washed with a little ether, and dried. 75.8 g (88% of the theoretical figure) of 4-(β-chloroethoxycarbonyl)amino-2-nitrophenyl tetrahydrofurfuryl ether are obtained with a melting point of 84°–86° C.

IR spectrum: see FIG. 4.

C. Preparation of 4-(β-hydroxyethyl)amino-2-nitrophenyl tetrahydrofurfuryl ether as intermediate III:

68.9 g of the 4-(β-chloroethoxycarbonyl)amino-2-nitrophenyl tetrahydrofurfuryl ether obtained above under B. are introduced, at 50° C., into a mixture of 60 g of 40% by weight aqueous sodium hydroxide solution and 150 ml of ethanol, during which the temperature increases from 50° C. to 58° C. The mixture is then stirred without further heating for 30 minutes, and then the pH is adjusted to 8 with concentrated hydrochloric acid, the mixture is filtered, the filtrate is evaporated to dryness, and the residue is taken up in ethanol to remove residual salts, the mixture is again filtered, and the solvent is removed in vacuo and, in this way, 56 g (99% of the theoretical figure) of 4-(β-hydroxyethyl)amino-2-nitrophenyl tetrahydrofurfuryl ether are obtained in the form of an orange-red oil.

IR spectrum: see FIG. 5.

D. Preparation of 2-amino-4-(β-hydroxyethyl)aminophenyl tetrahydrofurfuryl ether:

The orange-red oil obtained above under C. is transferred with 160 ml of ethanol into a stainless steel autoclave, about 1 g of Raney nickel catalyst is added, and catalytic reduction is carried out within 4 hours at 70° C. and under a hydrogen pressure of 80 bar. After removal of the catalyst, the reaction solution is acidified with sulphuric acid under nitrogen, and the product is isolated as the sulphuric acid salt ($\times \frac{1}{2}H_2SO_4$).

Yield: 36 g (59.8% of theory).

IR spectrum: see FIG. 12.

EXAMPLE 5

Preparation of 4-amino-2-methylaminophenyl tetrahydrofurfuryl ether

A. Preparation of 2-methylamino-4-nitrophenyl tetrahydrofurfuryl ether as intermediate:

23.8 g of 2-amino-4-nitrophenyl tetrahydrofurfuryl ether of the formula III are dissolved in 200 ml of 1,2-dimethoxyethane and, at 60° C., 5 g of sodium carbonate and 9 g of dimethyl sulphate are added on each of three occasions within 8 hours. The mixture is then stirred at 60° C. for 8 hours, and the inorganic salts are removed at elevated temperature and are extracted by boiling with 200 ml of ethanol, and the filtrates are combined, evaporated to dryness in vacuo, and the remaining deep yellow oil is triturated several times with warm water, carefully separated off and dried.

Yield: 21 g (83% of the theoretical figure).

IR spectrum: see FIG. 8.

B. Preparation of 4-amino-2-methylaminophenyl tetrahydrofurfuryl ether:

The oil obtained above under A. is catalytically reduced under the conditions described in Example 3, stage D., within 90 minutes, and the title product is precipitated by addition of sulphuric acid and is isolated as the sulphuric acid salt ($\times \frac{1}{2}H_2SO_4$).

Yield: 12.6 g (55.8% of theory).
Melting point: 140° C.
IR spectrum: see FIG. 13.

EXAMPLE 6

Preparation of 4-bis-($\beta$-hydroxyethyl)amino-2-aminophenyl tetrahydrofurfuryl ether Preparation of 4-bis-($\beta$-hydroxyethyl)amino-2-nitrophenyl tetrahydrofurfuryl ether as intermediate:

Gaseous ethylene oxide is passed through a solution of 119 g of 4-amino-2-nitrophenyl tetrahydrofurfuryl ether of the formula V in 400 ml of water at 70° C. until reaction is complete. The mixture is cooled to room temperature, the aqueous phase is decanted off, and the oily product is washed twice with 100 ml of water and dried in vacuo.

Yield: 151.6 g (93% of the theoretical figure).
IR spectrum: see FIG. 9.

Preparation of 4-bis-($\beta$-hydroxyethyl)amino-2-aminophenyl tetrahydrofurfuryl ether:

65.2 g of the intermediate obtained in stage A. are catalytically reduced under the conditions mentioned in stage D. of Example 3. After removal of the catalyst, 40 ml of concentrated hydrochloric acid are added to the ethanolic reaction solution under nitrogen, and the mixture is evaporated to dryness in a rotary evaporator. 50 g (67.8% of theory) of the desired product are obtained in the form of the dihydrochloride.

Melting point: 163°–165° C.
IR spectrum: see FIG. 14.

EXAMPLE 7

Preparation of 2,4-bis-($\beta$-hydroxyethylamino)phenyl tetrahydrofurfuryl ether Preparation of 2,4-bis-($\beta$-chloroethoxycarbonylamino)-phenyl tetrahydrofurfuryl ether as intermediate:

104 g of 2,4-diaminophenyl tetrahydrofurfuryl ether, obtained as stated in Example 2 (liberated from the sulphate), and 52 g of calcium carbonate are initially introduced into 300 ml of 1,2-dimethoxyethane under nitrogen and, at 80° C., 145 g of $\beta$-chloroethyl chloroformate are added within 1 hour. The reaction mixture is then stirred under reflux for 1 hour, poured onto 1 l of ice-water, and the product is filtered off. It is washed with water, dried and recrystallized from toluene.

Yield: 152 g (72.2% of theory).
Melting point: 84°–85° C.

Preparation of 2,4-bis-($\beta$-hydroxyethylamino)phenyl-tetrahydrofurfuryl ether:

106 g of the intermediate obtained in Stage A. are initially introduced into 250 ml of water and, at 75°–80° C., 175 g of 50% strength aqueous potassium hydroxide solution are added within 40 minutes. The mixture is then left to stir at 75° C. for 45 minutes, cooled to 60° C., the pH is reduced to 8 with glacial acetic acid, and the mixture is cooled further to 10° C., the oily product is separated from the aqueous phase, taken up in 250 ml of ethanol, and 50 ml of concentrated hydrochloric acid are added. After evaporation to dryness, 77.5 g (84.0% of the theoretical figure) of a highly hydroscopic dihydrochloride are obtained, and this is immediately incorporated in a hair tinting agent.

EXAMPLE 8

Preparation of 4-amino-2-($\beta$-dimethylaminoethyl)aminophenyl tetrahydrofurfuryl ether A. Preparation of N-(2-tetrahydrofurfuryloxy-5-nitrophenyl) oxazolidone-(2) as intermediate I:

137.8 g of 2($\beta$-chloroethoxycarbonyl)amino-4-nitrophenyltetrahydrofurfuryl ether (obtained as stated in Example 3, stage B.) are initially introduced into 250 ml monoethyleneglycol dimethylether and, at 40°–45° C., added with 45 g of 50% strength aqueous potassium hydroxide solution within 45 minutes. The mixture is then left to stir at 45° C. for 2 hours, 300 g of ice-water is added and the residual product is removed with suction. It is washed twice with 100 ml water each time and dried in vacuo.

Yield: 119.5 g (97% of the theoretical figure).
Melting point: 140° C.

B. Preparation of 2($\beta$-bromoethyl)amino-4-nitrophenyl tetrahydrofurfuryl ether as intermediate II:

67.8 g of the N-(2-tetrahydrofurfuryloxy-5-nitrophenyl)oxazolidone-(2) obtained under stage A are introduced in portions into 230 g of 48 percent hydrobromic acid, the temperature being maintained at 90° C. The mixture is left to stir at this temperature for 4 hours, cooled down slowly, and the precipitated hydrobromide is separated off, washed twice with 48 percent hydrobromic acid of 20 ml each, solved at 75° C. in 220 ml water. The pH of the solution is set with ammonia to 7.0 and the solution is then slowly cooled down by stirring. A precipitate of the product as stated in the title is obtained. It is removed by suction, washed twice with water of 30 ml each and dried.

Yield: 54 g (71.1% of the theoretical figure).
Melting point: 74°–75° C.
IR spectrum: see FIG. 15.

C. Preparation of 2($\beta$-dimethylaminoethyl)amino-4-nitrophenyl tetrahydrofurfuryl ether as intermediate III:

27.6 g of the product 2-($\beta$-bromoethyl)amino-4-nitrophenyl tetrahydrofurfuryl ether prepared as stated in stage B are combined with 60 ml of a 40 percent aqueous dimethylamine solution and heated to 60° C. for 30 minutes. Then 300 ml ice-water are added, the pH is adjusted to 8.8 with glacial acetic acid, the remaining oily product is crystallized, removed by suction and washed twice with 50 ml water each time and dried at 40° C. in vacuo.

Yield: 19 g (76.8% of the theoretical figure).
Melting point: 58° C.
IR spectrum: see FIG. 16.

D. Preparation of 4-amino-2-($\beta$-dimethylaminoethyl)aminophenyl tetrahydrofurfuryl ether:

19 g of the intermediate III prepared according to C. are transferred together with 180 ml of methanol into a stainless steel autoclave, about 0.5 g of Raney nickel catalyst is added, and catalytic reduction is carried out within 2 hours at 60° C. and under hydrogen pressure of 80 bar. After removal of the catalyst, the reaction solution is acidified with the calculated amount of sulphuric acid under nitrogen and the product stated in the title is obtained by this as an oily semi-sulfate which crystallizes within 48 hours. It is isolated, triturated with 100 ml ether in a mortar, filtered off with suction, washed twice with 50 ml ether each time and dried.

Yield: 11.3 g (56% of the theoretical figure).

Melting point: 93° C.
IR spectrum: see FIG. 17.

EXAMPLE 9

Preparation of 4-amino-2-(β-bromoethyl)aminophenyl tetrahydrofurfuryl ether 46.2 g N-(2-tetrahydrofurfuryloxy-5-nitrophenyl)-oxazolidone-(2) (obtained according to Example 8, stage A) are transferred with 400 ml methanol into a stainless steel autoclave, mixed with approximately 1 g of Raney nickel catalyst and reduced at 60° C. within 5 hours under hydrogen pressure of 80 bar. After removal of the catalyst, the reaction solution is acidified with some 48 percent hydrobromic acid, and the solvent is entirely removed in vacuo. The remaining oil is heated together with 150 g of 48 percent hydrobromic acid for 3 hours at 90° C. and the lightly brownish solution is evaporated almost completely to dryness in vacuo at about 50° C. The residue obtained in this manner is pressed off on a frit, mixed threetimes with 30 ml ethanol and removed by sunction each time and finally dried.

Yield: 60.8 g of the dihydrobromide of the product stated in in the title (85% of the theoretical figure).

Melting point: >210° C.

IR spectrum: see FIG. 18.

The hair tinting agents according to the invention, which contain the compounds of the general formula VIII as coupling components and developing substances which are generally used for oxidation hair tinting, are distinguished by high stability on storage and they provide on use very intense colour shades, ranging from red-brown to blue-black, with good fastness properties of the tintings obtained therewith.

When hair tinting agents are used, the coupling component is generally used in approximately molar amounts relative to the developing substances used. Even if use of molar amounts proves advantageous, it is nevertheless not disadvantageous if a certain amount more or less than the molar amount of the coupling component is used.

The compounds of the general formula VIII which are to be used according to the invention as coupling components can be used either as such or in the form of their salts with inorganic or organic acids, such as, for example, as chlorides, sulphates, phosphates, acetates, propionates, lactates or citrates.

New coupling substances of the general formula VIII, of which 2,4-diaminophenyl tetrahydrofurfuryl ether is preferred, should be present in the hair tinting agents according to the invention in a concentration of about 0.001 to 5.0% by weight and in particular of 0.2 to 3.0% by weight.

Furthermore, it is unnecessary to use just one developing component; on the contrary it is also possible to use a mixture of different developing compounds.

Examples of developing components which are to be used and which may be listed are primary aromatic or heteroaromatic amines having another functional group located in the p-position, such as p-phenylenediamine, p-toluylenediamine, p-aminophenol, N,N-dimethyl-p-phenylenediamine, chloro-p-phenylenediamine, methoxy-p-phenylenediamine, 2,5-diaminopyridine and their derivatives, and other compounds of the type mentioned which additionally carry one or more functional groups, such as OH groups, $NH_2$ groups, NHR groups or NRR groups, R representing an optionally substituted alkyl radical having 1 to 4 carbon atoms.

Furthermore, it is unnecessary to use just the coupling components of the general formula VIII according to the invention; on the contrary, it is also possible, in order to obtain particular colour shades, to use other coupling components which are already known and used, such as, for example, α-naphthol, 3,4-diaminobenzoic acid, resorcinol, 4-chlororesorcinol, m-aminophenol, m-phenylenediamine, m-toluylenediamine, 2,4-diaminoanisole, catechol, pyrogallol, 1,5- or 1,7-dihydroxynaphthalene, 5-amino-2-methylphenol, 6-amino-2-methylphenol or derivatives of the said compounds.

In addition, the hair tinting agents can optionally contain customary direct dyes if this is necessary to obtain particular colour shades. The oxidative coupling, that is to say the development of the tinting, can also be brought about by atmospheric oxygen, as in principle with other oxidation dyes. However, it is more advantageous to use chemical oxidizing agents.

The hair tinting agents according to the invention are aqueous agents. These are defined as all agents which contain water in any way whatsoever, such as, for example, creams, emulsions, gels or even simple solutions. The composition of the hair tinting agent represents a mixture of the dyeing components with the additives customary for cosmetic preparations of this type.

Examples of customary additives in solutions, creams, emulsions or gels are solvents such as water, lower aliphatic alcohols, for example ethanol, propanol and isopropanol, or glycols such as glycerol and glycol ethers, such as propylene glycol, furthermore wetting agents or emulsifiers from the classes of anionic, cationic, amphoteric or non-ionic surface-active substances such as fatty alcohol sulphates, alkylsulphonates, alkylbenzenesulphonates, alkyltrimethylammonium salts, alkylbetaines, oxyethylated fatty alcohols, oxyethylated nonylphenols, fatty acid alkanolamides, oxyethylated fatty acid esters, furthermore thickening agents such as higher fatty alcohols, starch, cellulose derivatives, vaseline, liquid paraffin and fatty acids.

The constituents which have been mentioned are used in amounts customary for such purposes, for example the wetting agents and emulsifiers in concentrations of about 0.5 to 30% by weight, whereas the thickening agents may be present in the preparations in an amount of about 0.1 to 25% by weight.

Depending on the composition, the hair tinting agents according to the invention can have a weakly acid, neutral or alkaline reaction. In particular, they have a pH in the alkaline range, between 7.5 and 11.5, this being adjusted with, preferably, ammonia. However, it is also possible to use organic amines, for example monoethanolamine and triethanolamine, or even inorganic bases such as sodium hydroxide and potassium hydroxide.

In processes for the oxidative tinting of hair, the hair tinting agents of this invention, which contain a combination of developing substances known in hair tinting with at least one compound of the general formula VIII, preferably 2,4-diaminophenyl tetrahydrofurfuryl ether, as coupling substance together with, where appropriate, additional known coupling substances and direct dyes, are mixed shortly before use with an oxidizing agent, and this mixture is applied to the hair. Oxidizing agents suitable for development of the hair tinting are mainly hydrogen peroxide, for example as a 6% strength aqueous solution, and its addition compounds to urea, melamine or sodium borate, as well as mixtures of hydrogen peroxide addition compounds of this type with potassium peroxodisulphate. The temperatures for use of these range from 15° to 40° C. After a time of about 30 minutes to act, the hair tinting agent is removed by rinsing from the hair which is to be tinted. Thereafter the hair is washed with a mild shampoo and is dried.

The example which follow are intended to illustrate the subject-matter of the invention in detail but not to restrict it to them.

| Example A | Hair tinting solution |
|---|---|
| 0.80 g | 2,4-diaminophenyl tetrahydrofurfuryl ether (x ½ $H_2SO_4$) |
| 0.15 g | χ-naphthol |
| 0.65 g | p-aminophenol |
| 2.00 g | oleic acid |
| 10.00 g | lauryl alcohol-diglycol ether sulphate, sodium salt (28% strength, aqueous solution) |
| 10.00 g | isopropanol |
| 0.50 g | sodium sulphite, anhydrous |
| 10.00 g | ammonia, 25% strength |
| 65.90 g | water |
| 100.00 g | |

60 g of the abovementioned hair tinting solution are mixed shortly before use with 60 g of hydrogen peroxide solution, 6% strength, and applied to naturally blond hair. After a time of 30 minutes to act at 40° C., and after rinsing, shampooing and drying the hair it has a acquired a deep mahogany tint.

| Example B | Hair tinting agent in the form of a cream |
|---|---|
| 0.40 g | 5-amino-2-methylphenol |
| 0.15 g | 2-($\beta$-hydroxyethylamino)-4-aminophenyl tetrahydrofurfuryl ether (× ½ $H_2SO_4$) |
| 0.95 g | 2,5-diaminotoluene (× $H_2SO_4$) |
| 2.00 g | oleic acid |
| 0.10 g | polyacrylic acid |
| 0.50 g | sodium sulphite, anhydrous |
| 3.50 g | lauryl alcohol-diglycol ether sulphate, sodium salt (28% strength aqueous solution) |
| 15.00 g | cetyl alcohol |
| 77.40 g | water |
| 100.00 g | |

50 g of the abovementioned hair tinting agent are mixed shortly before use with 50 g of hydrogen peroxide solution, 6% strength. The mixture is allowed to act on naturally blond hair at 40° C. for 30 minutes. Then the tinting composition is rinsed out, and the hair is shampooed and dried. It has acquired a full and deep aubergine shade.

In the examples compiled below in Table II, the compounds of the general formula VIII according to the invention were used for the various colourings as coupling component with different developing substances.

The following compounds were used as coupling substances:

K1: 2,4-Diaminophenyl tetrahydrofurfuryl ether
K2: 2-($\beta$-Hydroxyethylamino)-4-aminophenyl tetrahydrofurfuryl ether
K3: 2-Amino-4-($\beta$-hydroxyethylamino)-phenyl tetrahydrofufuryl ether
K4: 2-(Methylamino)-4-aminophenyl tetrahydrofurfuryl ether
K5: 2-Amino-4-bis-($\beta$-hydroxyethyl)aminophenyl tetrahydrofurfuryl ether
K6: 2,4-bis-($\beta$-hydroxyethylamino)-phenyl tetrahydrofurfuryl ether
K7: 4-amino-2-($\beta$-dimethylaminoethyl)aminophenyl tetrahydrofurfuryl ether
K8: 4-amino-2-($\beta$-bromoethyl)aminophenyl tetra hydrofurfuryl ether The following compounds were used as developing substances:

E1: p-Phenylenediamine
E2: p-Toluylenediamine
E3: p-Aminophenol
E4: Chloro-p-phenylenediamine
E5: Methoxy-p-phenylenediamine
E6: N,N-Dimethyl-p-phenylenediamine
E7: 4,4'-Diaminodiphenylamine
E8: p-Amino-diphenylamine
E9: 4-Methylamino-phenol
E10: Colour developer 4
E11: Colour developer 3
E12: 4-Amino-2-methylphenol The hair tinting agents according to the invention for which the colouring results are indicated in Table II were used as cream emulsions. This entailed 0.008 mole of each of the abovementioned developing and coupling substances being incorporated in a cream composed of
8 parts by weight of fatty alcohol ($C_{12}$–$C_{18}$)
12 parts by weight of fatty alcohol sulphate (Na salt)
70 parts by weight of water
Then the pH of the cream was adjusted to 10 using ammonia, and the mixture was made up to 100 parts by weight with water.

The oxidative coupling was carried out with 3% strength hydrogen peroxide solution as the oxidizing agent, 40 g of the hydrogen peroxide solution being added as oxidizing agent to 40 g of the cream. Each tinting cream was applied to human hair which was 90% grey, and was left in place for 30 minutes. After this time had elapsed it was washed out with a customary hair shampoo, and the hair was then dried. The tints obtained by this are shown in Table II below.

TABLE II

Results of colouring with hair tinting agents which contain the indicated coupling and developing components.

| Coupling component | Developing component | Tint obtained |
|---|---|---|
| K 1 | E 2 | dark blue |
| K 1 | E 3 | mahogany red |
| K 1 | E 4 | dark violet |
| K 1 | E 9 | brick red |
| K 1 | E 11 | dark blue-green |
| K 2 | E 2 | dark blue |
| K 2 | E 8 | steel blue |
| K 2 | E 12 | yellow-brown |
| K 2 | E 6 | royal blue |
| K 3 | E 1 | blue-black |
| K 3 | E 5 | dark violet-blue |
| K 3 | E 4 | dark violet |
| K 3 | E 10 | royal blue |
| K 3 | E 11 | steel blue |
| K 4 | E 7 | matt dark blue |
| K 4 | E 1 | blue-black with violet reflections |
| K 4 | E 3 | chestnut |
| K 4 | E 8 | blue-grey |
| K 5 | E 5 | stone grey |
| K 5 | E 1 | dark violet |
| K 5 | E 6 | matt blue-green |
| K 1 | E 8 | dark yellow-green |
| K 1 | E 7 | blue-black |
| K 1 | E 6 | blue-black |
| K 6 | E 3 | pink |
| K 6 | E 1 | dark blue with violet tinge |

TABLE II-continued

Results of colouring with hair tinting agents which contain the indicated coupling and developing components.

| Coupling component | Developing component | Tint obtained |
|---|---|---|
| K 7 | E 1 | dark brown with violet tinge |
| K 7 | E 3 | chestnut |
| K 7 | E 4 | grey violet |
| K 8 | E 1 | dark brown |
| K 8 | E 3 | fawn-brown |
| K 8 | E 4 | chestnut |

BRIEF DESCRIPTION OF THE DRAWINGS

The drawings

FIG. 1—2,4-Dinitrophenyl tetrahydrofurfuryl ether of the formula II according to Example 2, A.1.

FIG. 2—2-Amino-4-nitrophenyl tetrahydrofurfuryl ether of the formula III according to Example 3, A.

FIG. 3—4-Amino-2-nitrophenyl tetrahydrofurfuryl ether of the formula V according to Example 4, A.2.

FIG. 4—4-($\beta$-Chloroethoxycarbonyl)amino-2-nitrophenyl tetrahydrofurfuryl ether according to general formula X and Example 4, B.

FIG. 5—4-($\beta$-Hydroxyethyl)amino-2-nitrophenyl tetrahydrofurfuryl ether according to general formula VI and Example 4, C.

FIG. 6—2-($\beta$-Chloroethoxycarbonyl)amino-4-nitrophenyl tetrahydrofurfuryl ether according to general formula IX and Example 3, B.

FIG. 7—2-($\beta$-Hydroxyethyl)amino-4-nitrophenyl tetrahydrofurfuryl ether according to general formula IV and Example 3, C.

FIG. 8—2-Methylamino-4-nitrophenyl tetrahydrofurfuryl ether according to general formula IV and Example 5, A.

FIG. 9—4-Bis-($\beta$-hydroxyethyl)-amino-2-nitrophenyl tetrahydrofurfuryl ether according to general formula VI and Example 6, A.

FIG. 10—2,4-Diaminophenyl tetrahydrofurfuryl ether of the formula XI ($\times \frac{1}{2}$ H$_2$SO$_4$) according to Example 2, B.

FIG. 11—4-Amino-2-($\beta$-hydroxyethyl)aminophenyl tetrahydrofurfuryl ether according to general formula XII ($\times \frac{1}{2}$ H$_2$SO$_4$) and Example 3, D.

FIG. 12—2-Amino-4-($\beta$-hydroxyethyl)aminophenyl tetrahydrofurfuryl ether according to general formula XIV ($\times \frac{1}{2}$ H$_2$SO$_4$) and Example 4, D.

FIG. 13—4-Amino-2-methylaminophenyl tetrahydrofurfuryl ether according to general formula XII ($\times \frac{1}{2}$ H$_2$SO$_4$) and Example 5, B.

FIG. 14—4-Bis-($\beta$-hydroxyethyl)amino-2-aminophenyl tetrahydrofurfuryl ether according to general formula XIV ($\times$2HCl) and Example 6, B.

FIG. 15—2-($\beta$-bromoethyl)amino-4-nitrophenyl tetrahydrofurfuryl ether according to general formula IV and Example 8, B.

FIG. 16—2-($\beta$-dimethylaminoethyl)amino-4-nitrophenyl tetrahydrofurfuryl ether according to general formula IV and Example 8, C.

FIG. 17—4-amino-2-($\beta$-dimethylaminoethyl)aminophenyl tetrahydrofurfuryl ether according to general formula XII ($\times \frac{1}{2}$ H$_2$SO$_4$) and Example 8, D.

FIG. 18—4-amino-2-($\beta$-bromoethyl)aminophenyl tetrahydrofurfuryl ether according to general formula XII ($>$2 HBr) and Example 9.

Figure 1:
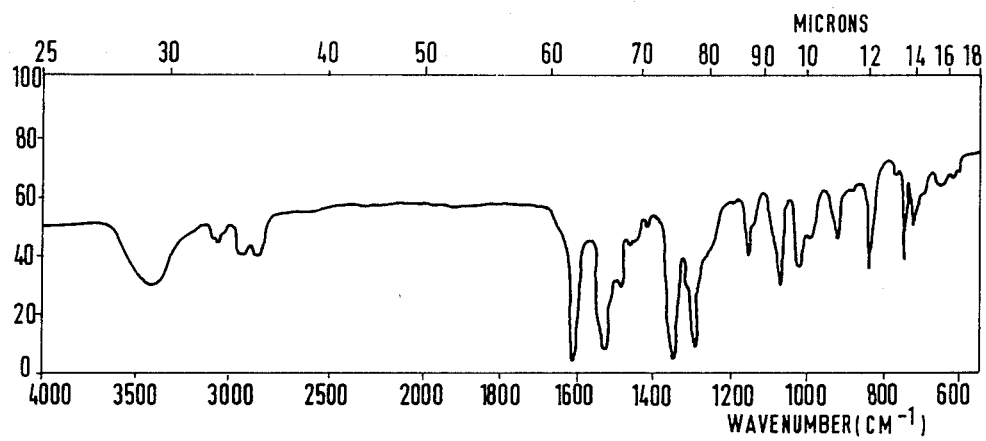
FIGS. 1 to 18 show the infrared absorption spectra of the following compounds.
Figure 2:
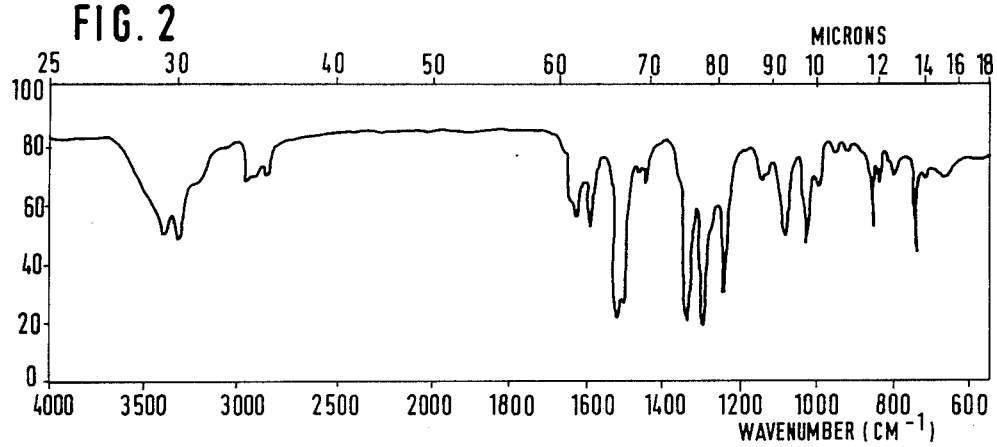
Figure 3:
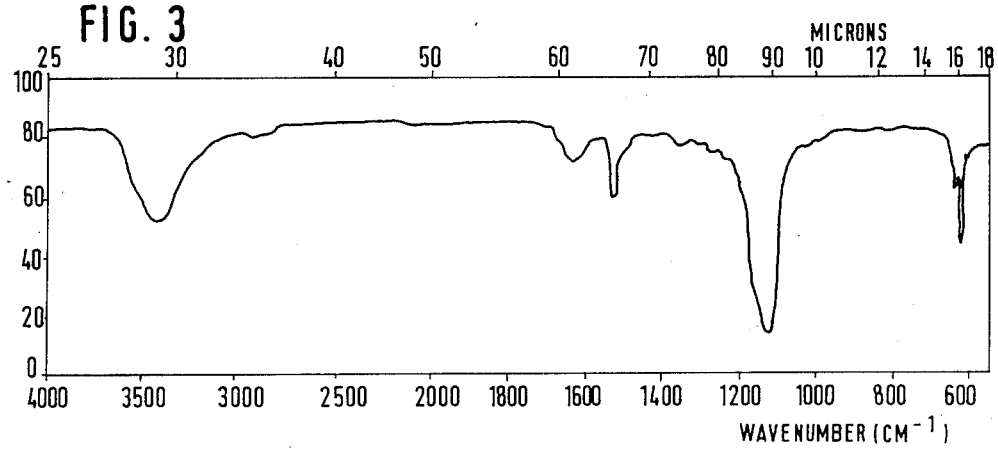
Figure 4:
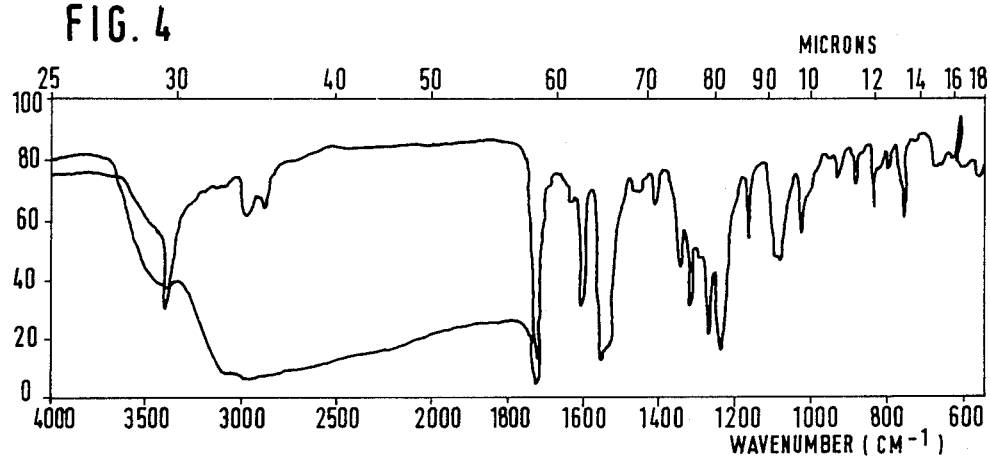
Figure 5:
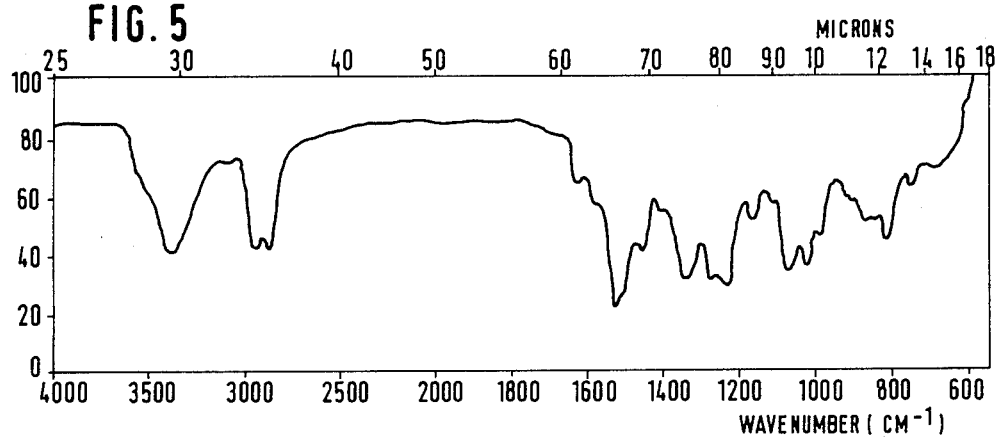
Figure 6:
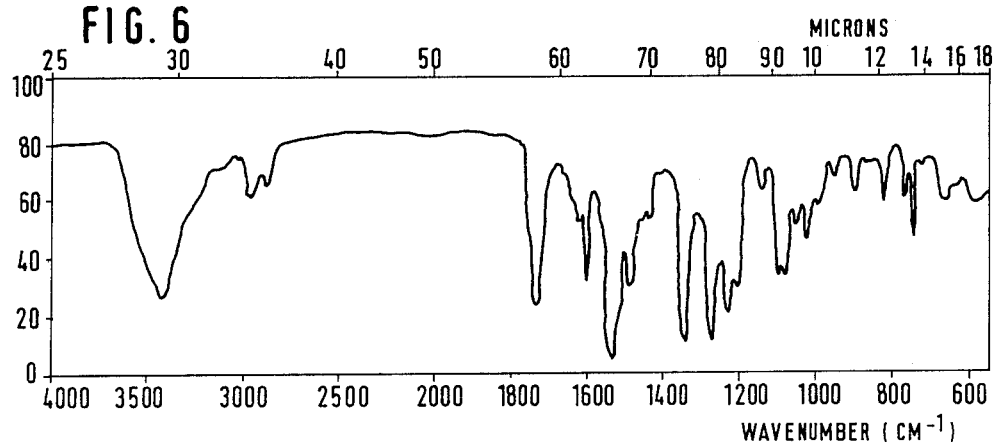
Figure 7:
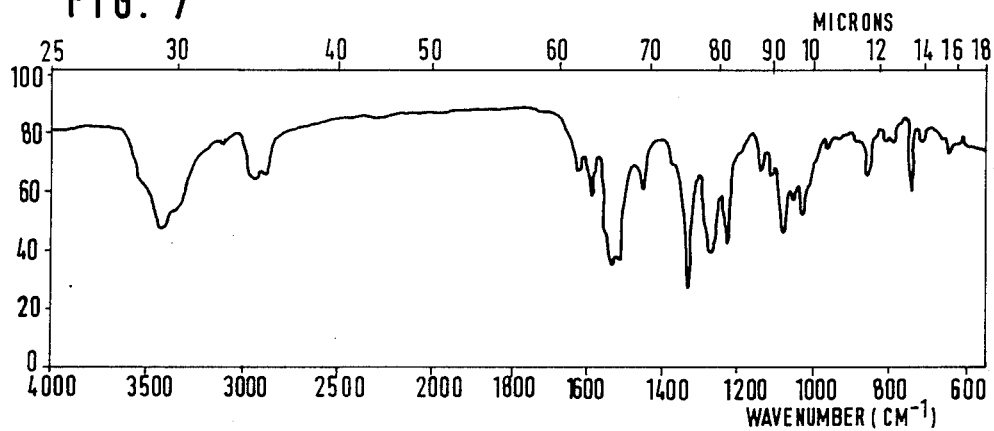
Figure 8:
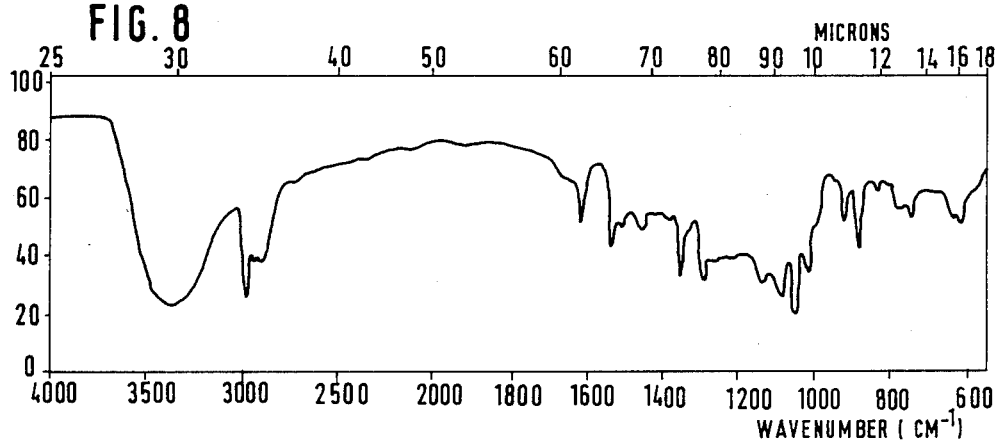
Figure 9:
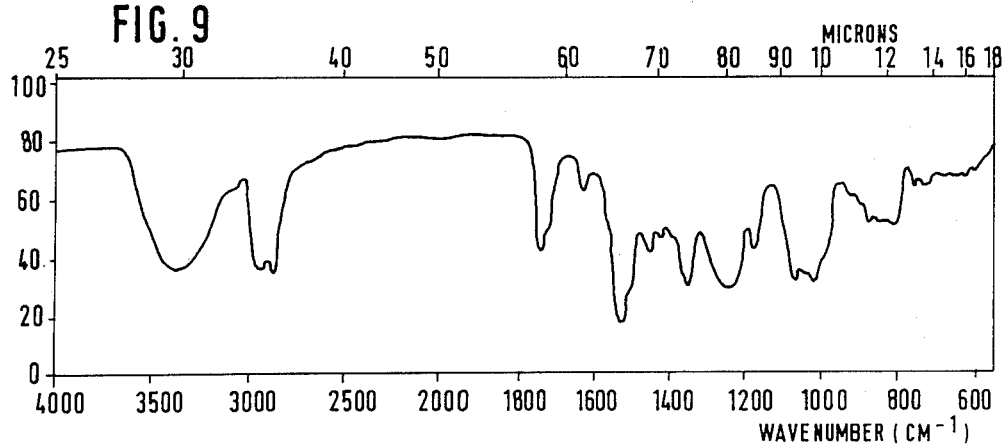
Figure 10:
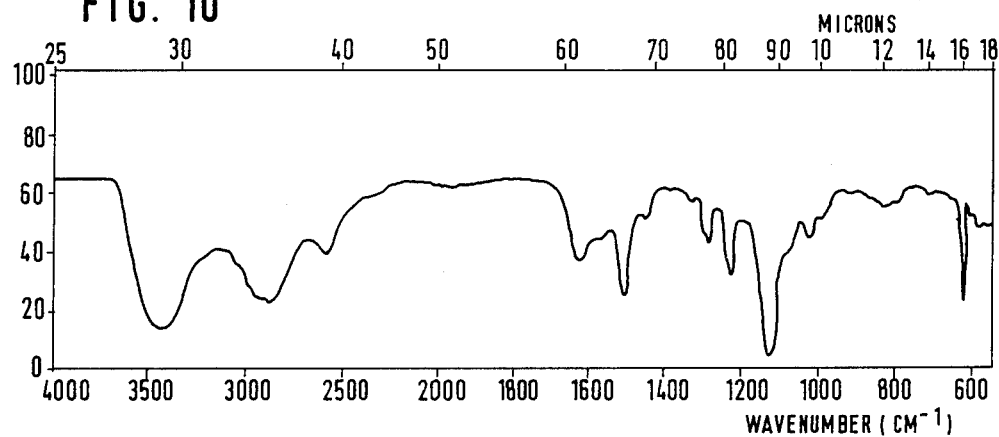
Figure 11:
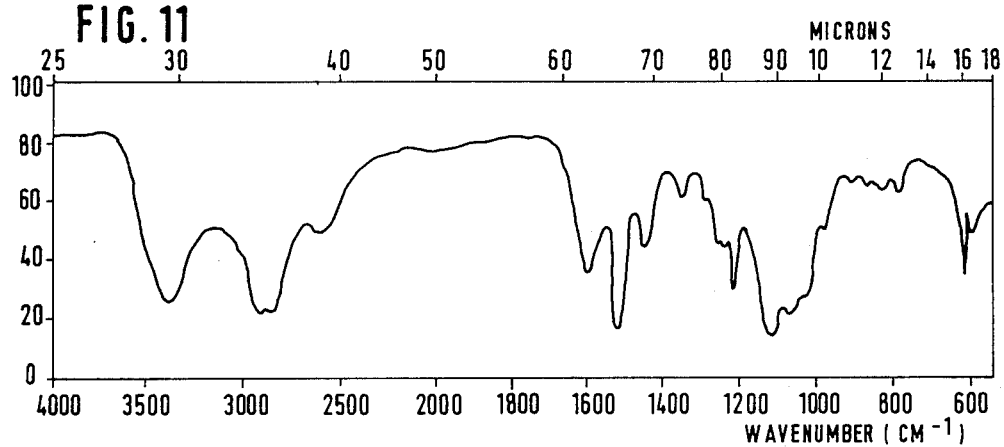
Figure 12:
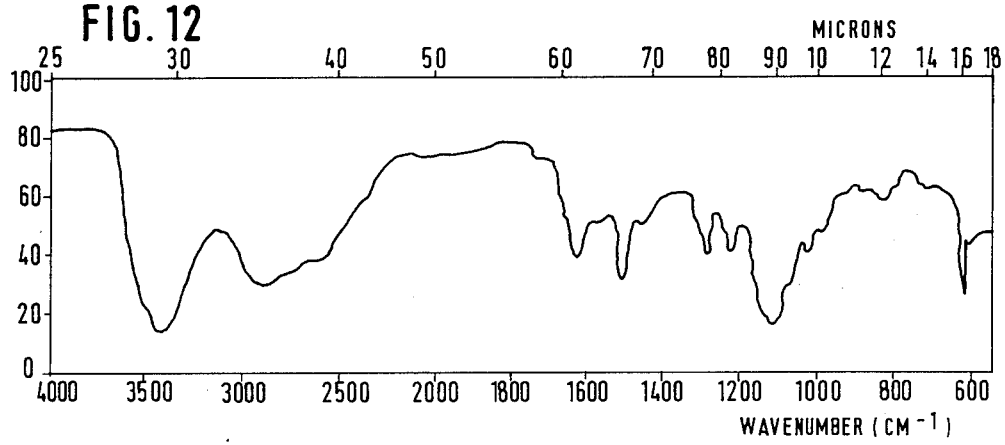
Figure 13:
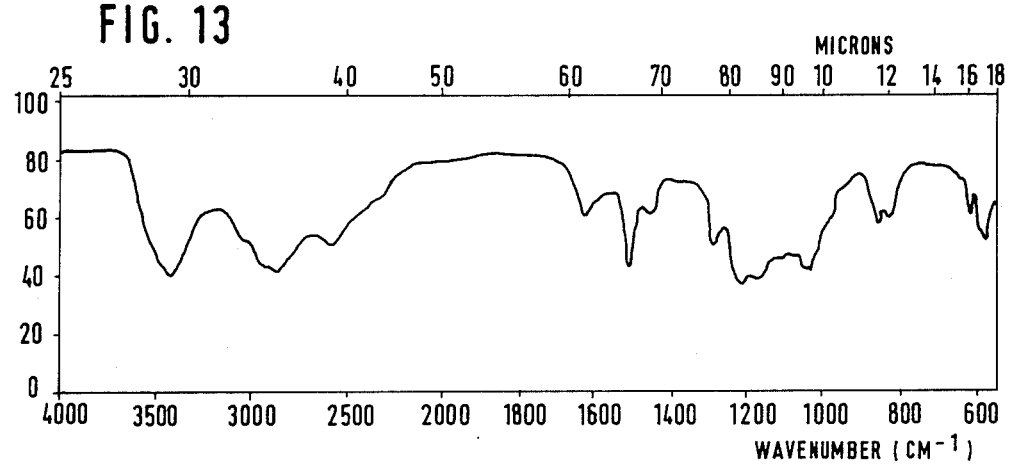
Figure 14:
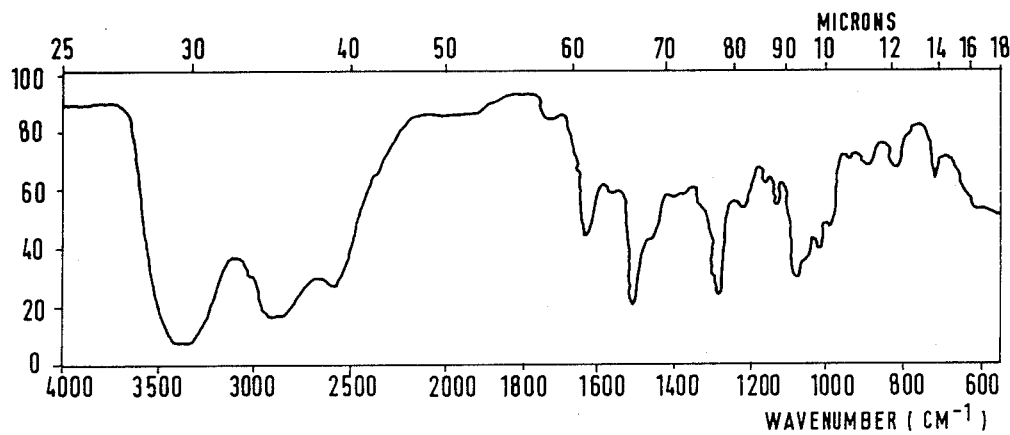
Figure 15:
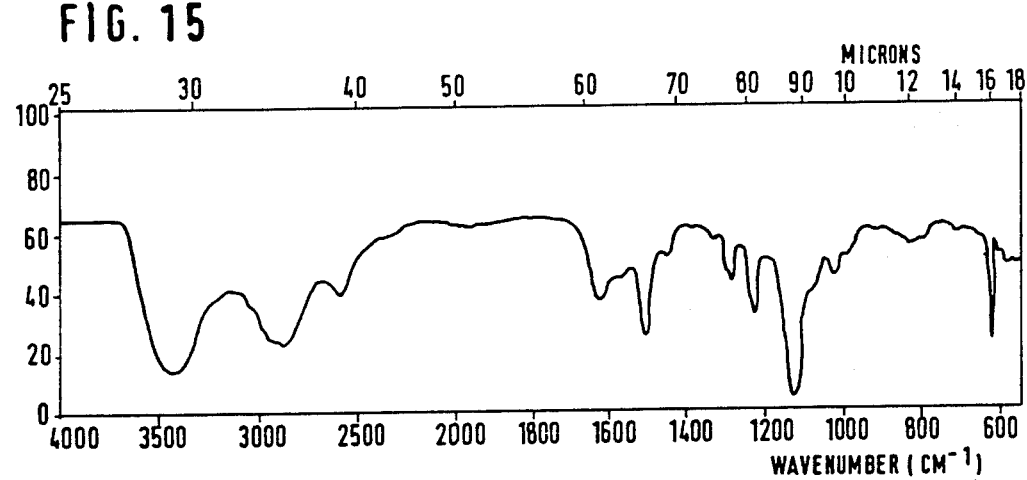
Figure 16:
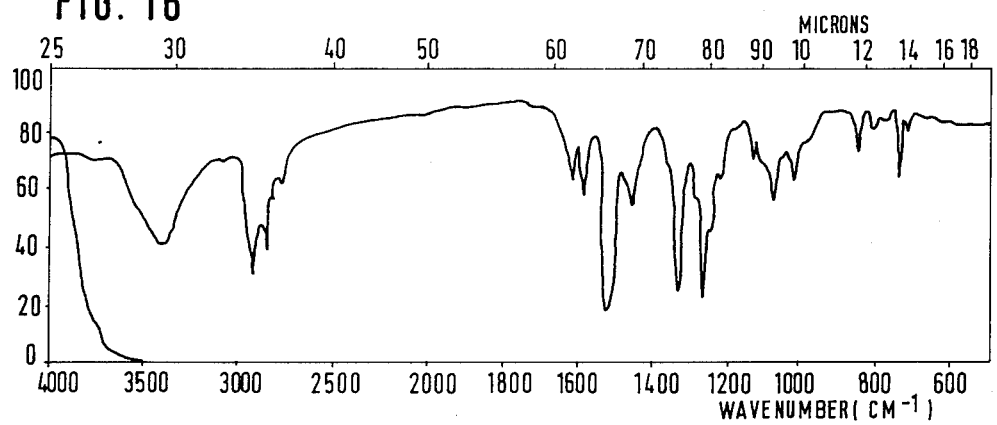
Figure 17:
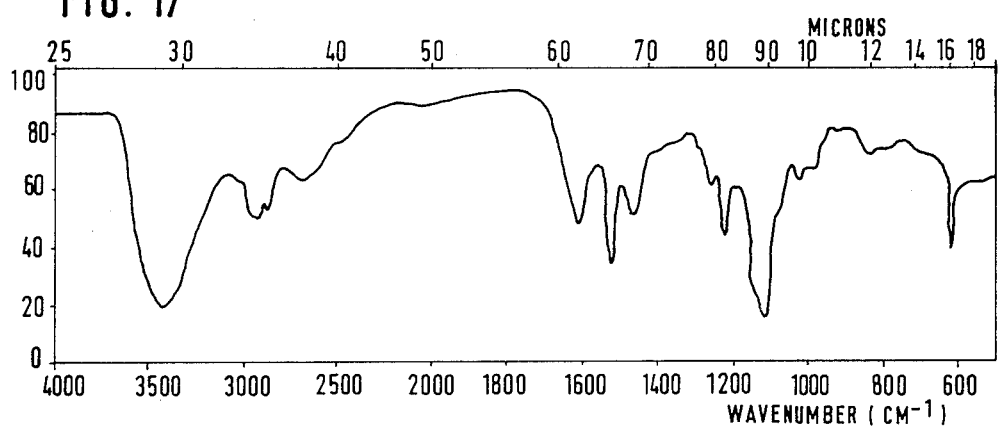
Figure 18:
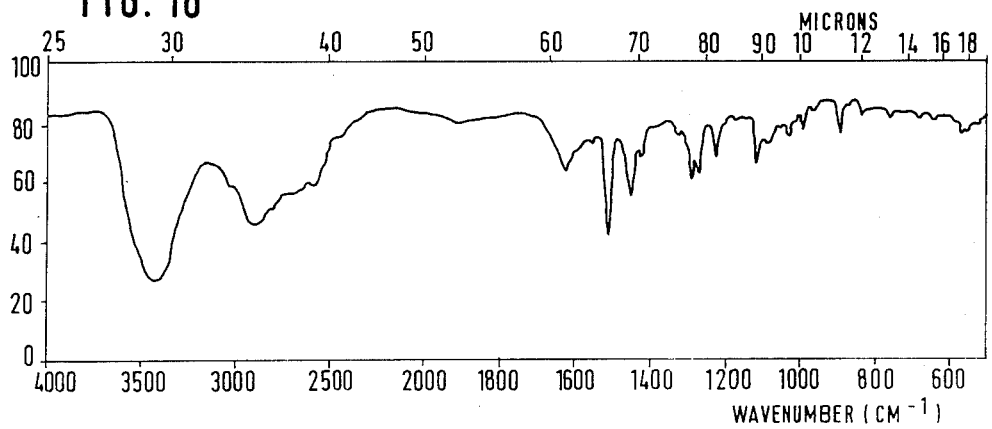

We claim:

1. A 2,4-Diaminophenyl tetrahydrofurfuryl ether of the formula VIII or a salt thereof with an inorganic or organic acid or mixtures thereof,

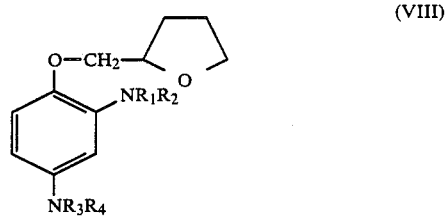

(VIII)

in which R$_1$, R$_2$, R$_3$ and R$_4$, independently of one another, each represent a hydrogen atom, a (C$_1$–C$_4$)-alkyl group, hydroxy(C$_2$–C$_4$)alkyl group, dihydroxy-(C$_3$–C$_4$)alkyl group, halogeno(C$_2$–C$_4$)alkyl group, amino(C$_2$–C$_4$)alkyl group or an amino(C$_2$–C$_4$)alkyl group which is substituted once or twice by methyl, ethyl or hydroxyethyl radicals on the nitrogen, the carbon chain being straight or branched, and it being a proviso that at least one of R$_1$, R$_2$, R$_3$ and R$_4$ represents a hydrogen atom.

2. A substituted 2,4-diaminophenyl tetrahydrofurfuryl ether of the formula VIII, in which only two of R$_1$, R$_2$, R$_3$ and R$_4$ represent hydrogen atoms, according to claim 1.

3. A 2,4-diaminophenyl tetrahydrofurfuryl ether according to claim 1.

4. 2-($\beta$-Hydroxyethylamino)-4-aminophenyl tetrahydrofurfuryl ether according to claim 1.

5. 2-Amino-4-($\beta$-hydroxyethylamino)phenyl tetrahydrofurfuryl ether according to claim 1.

6. 2-Methylamino-4-aminophenyl tetrahydrofurfuryl ether according to claim 1.

7. 2-Amino-4-bis($\beta$-hydroxyethyl)aminophenyl tetrahydrofurfuryl ether according to claim 1.

8. An aqueous tinting dyeing composition for human hair comprising at least one coupler and an effective amount of at least one developing component, in which the coupler corresponds to the formula VIII or to a physiologically acceptable acid salt thereof

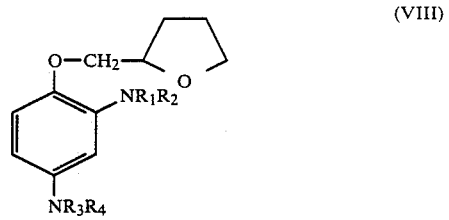

(VIII)

in which R$_1$, R$_2$, R$_3$ and R$_4$, independently of one another, each represent a hydrogen atom, a (C$_1$–C$_4$)alkyl group, hydroxy(C$_2$–C$_4$)alkyl group, dihydroxy(C$_3$–C$_4$)alkyl group, halogeno(C$_2$–C$_4$)alkyl group, amino(C$_2$–C$_4$)alkyl group or an amino(C$_2$–C$_4$)alkyl group which is substituted once or twice by methyl, ethyl or hydroxyethyl radicals on the nitrogen, the carbon chain being straight or branched, and it being a proviso that at least one of R$_1$, R$_2$, R$_3$ and R$_4$ represents a hydrogen atom.

9. A composition according to claim 8, which contains as a coupler the compound of the formula XI:

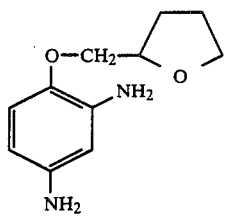 (XI)

or its acid salts.

10. A composition according to claim 8, in which the compound of the formula VIII makes up 0.001 to 5% by weight of the total composition.

11. The aqueous tinting dyeing composition according to claim 12 which additionally contains at least one additive or at least one auxiliary agent.

12. A composition according to claim 8, in which the coupler corresponds to the formula VIII or its acid salts, with the proviso that at least two of $R_1$, $R_2$, $R_3$ and $R_4$ are hydrogen atoms.

13. A compound as claimed in claim 1 which provides a blue color.

* * * * *